(12) United States Patent
Martin et al.

(10) Patent No.: US 11,191,877 B2
(45) Date of Patent: Dec. 7, 2021

(54) BIOSORBABLE ENDOPROSTHESIS

(71) Applicant: MAGNUS FLOW LIMITED, London (GB)

(72) Inventors: John Francis Martin, London (GB); Anthony Mathur, London (GB)

(73) Assignee: MAGNUS FLOW LIMITED, London (GB)

( * ) Notice: Subject to any disclaimer, the term of this patent is extended or adjusted under 35 U.S.C. 154(b) by 0 days.

(21) Appl. No.: 16/164,888

(22) Filed: Oct. 19, 2018

(65) Prior Publication Data

US 2019/0117854 A1  Apr. 25, 2019

Related U.S. Application Data

(63) Continuation of application No. 14/347,687, filed as application No. PCT/GB2012/052429 on Oct. 1, 2012, now abandoned.

(30) Foreign Application Priority Data

Sep. 30, 2011  (GB) .................................... 1116879

(51) Int. Cl.
| | | |
|---|---|---|
| A61F 2/06 | (2013.01) |
| A61L 27/58 | (2006.01) |
| A61L 31/14 | (2006.01) |
| A61L 31/00 | (2006.01) |
| A61L 31/02 | (2006.01) |
| A61L 31/08 | (2006.01) |
| A61L 31/18 | (2006.01) |

(52) U.S. Cl.
CPC .......... *A61L 31/148* (2013.01); *A61L 31/005* (2013.01); *A61L 31/022* (2013.01); *A61L 31/088* (2013.01); *A61L 31/18* (2013.01)

(58) Field of Classification Search
CPC ...... A61F 2/82; A61F 2/06; A61F 2250/0054; A61L 27/58
USPC ............................................... 623/1.15–1.48
See application file for complete search history.

(56) References Cited

U.S. PATENT DOCUMENTS

| | | | |
|---|---|---|---|
| 7,691,142 B2 | 4/2010 | Nissl | |
| 8,052,744 B2* | 11/2011 | Girton | A61L 31/146 623/1.39 |
| 8,236,046 B2* | 8/2012 | Weber | A61L 31/022 623/1.38 |
| 8,449,603 B2* | 5/2013 | Weber | A61L 31/088 623/1.48 |
| 2003/0100830 A1* | 5/2003 | Zhong | A61L 31/145 600/431 |
| 2004/0030379 A1* | 2/2004 | Hamm | A61K 31/335 623/1.15 |
| 2007/0244569 A1* | 10/2007 | Weber | A61L 31/148 623/23.75 |
| 2008/0071353 A1* | 3/2008 | Weber | A61L 31/148 623/1.15 |
| 2008/0086201 A1* | 4/2008 | Weber | A61P 9/10 623/1.42 |
| 2009/0123521 A1* | 5/2009 | Weber | A61L 27/30 424/426 |
| 2009/0240323 A1* | 9/2009 | Wilcox | A61L 31/10 623/1.38 |
| 2011/0276124 A1* | 11/2011 | Doerr | A61L 31/022 623/1.15 |
| 2011/0282436 A1* | 11/2011 | Rahi | A61L 31/082 623/1.42 |
| 2012/0141562 A1 | 6/2012 | Achneck et al. | |
| 2012/0143318 A1 | 6/2012 | Gulcher | |
| 2014/0213971 A1 | 7/2014 | Dolan et al. | |
| 2014/0324158 A1* | 10/2014 | Martin | A61P 7/02 623/1.38 |
| 2018/0085459 A1* | 3/2018 | Fahmy | A61K 35/44 |

FOREIGN PATENT DOCUMENTS

| | | |
|---|---|---|
| WO | WO 2003/065881 | 8/2003 |
| WO | WO 2004/093643 | 11/2004 |
| WO | WO 2005/056073 | 12/2004 |
| WO | WO 2008/034030 | 3/2008 |
| WO | WO 2008/034050 | 3/2008 |
| WO | WO 2010/145842 | 12/2010 |

OTHER PUBLICATIONS

Mangual et al., "Biodegradable nanocomposite magnetite stent for implant-assisted magnetic drug targeting," *Journal of Magnetism and Magnetic Materials*, 322(20):3094-3100, 2010.
Office Communication issued in U.S. Appl. No. 14/347,687, dated Apr. 19, 2018.
Office Communication issued in U.S. Appl. No. 14/347,687, dated Sep. 13, 2016.
Office Communication issued in U.S. Appl. No. 14/347,687, dated Mar. 28, 2016.
Office Communication issued in U.S. Appl. No. 14/347,687, dated Nov. 24, 2015.
PCT International Search Report and Written Opinion issued in International Application No. PCT/GB2012/052429, dated Feb. 27, 2013.
Pislaru et al., "Magnetically targeted endothelial cell localization in stented vessels," *Journal of the American College of Cardiology*, 48(9):1839-1845, 2006.
Polyak et al., "High field gradient targeting of magnetic nanoparticle-loaded endothelial cells to the surfaces of steel stents," *PNAS*, 105(2): 698-703, 2008.
Schinhammer et al., "Design strategy for biodegradable Fe-based alloys for medical applications," *Acta Biomater.*, 6(5):1705-1713, 2010.

\* cited by examiner

*Primary Examiner* — Suzette J Gherbi
(74) *Attorney, Agent, or Firm* — Parker Highlander PLLC

(57) ABSTRACT

A biosorbable magnetisable endoprosthesis, may be useful in the therapy of restenosis. A method for the treatment of prevention of restenosis or a disease of the coronary artery, comprises fitting a patent with an endoprosthesis according to the invention, which has either been magnetized prior to placement in the body or which is magnetized in situ, and administering to the patient magnetized cells capable of repairing an artery.

12 Claims, No Drawings

BIOSORBABLE ENDOPROSTHESIS

This application is a continuation of U.S. patent application Ser. No. 14/347,687, filed Mar. 27, 2014, which is a national phase application under 35 U.S.C. § 371 of International Application No. PCT/GB2012/052429, filed Oct. 1, 2012, which claims priority to United Kingdom Application No. 1116879.6, filed Sep. 30, 2011. The entire text of each of the above-referenced disclosures is specifically incorporated herein by reference.

FIELD OF THE INVENTION

This invention relates to endoprostheses, in particular to coronary stents and to their use in the prevention and treatment of disease of the coronary arteries after angioplasty.

BACKGROUND OF THE INVENTION

Cardiovascular disease is the largest cause of death in the UK. This condition is characterised by a disease process called atherosclerosis, which is a thickening and hardening of the coronary arteries supplying blood to the heart. This often leads to chest pain (partial obstruction of blood flow) or a heart attack (a complete obstruction of blood flow, which is fatal in 50% of cases). Obstructive narrowing due to atherosclerosis can be relieved by 'ballooning' open the narrowing and inserting a stainless steel scaffold (coronary artery stent, which may also be used to stent other 'tubes' in the body) to prevent the narrowing from returning. This procedure, termed percutaneous angioplasty and stent insertion, is performed under local anaesthetic, and is considered routine in the treatment of people with heart disease.

After angioplasty and stent insertions, narrowing of the coronary arteries returns in up to 30% of people. This process, i.e. restenosis, occurs within the stent itself. As part of the body's natural healing process, a functional endothelial layer is formed over the stent. This may be a relatively slow process, however, and can allow scar tissue to build up over the stent (restenosis). Various methods have been used to try to reduce this complication. The emergence of drug-eluting stents (coated with an anti-cancer agent) has dramatically reduced the incidence of in-stent restenosis. This therapy interferes with the natural healing response by preventing, the "scarring" process around the stent and therefore delays restenosis. Although more expensive than conventional stents, the improvement in long-term outcome leads to a reduction in overall costs in certain patients. However, this delay in healing can also lead to the formation of blood clots within the stent. This can completely stop blood supply and cause a heart attack.

Recently, the existence of circulating endothelial progenitor cells (EPCs) has been identified as a key factor for re-endothelialisation. While delaying the formation of a functional endothelial layer may prevent restenosis (as the formation of scar tissue is also delayed), the early establishment of a functional endothelial layer after vascular injury has been shown to assist in the prevention of neointimal proliferation (restenosis process) and thrombus formation (blood clot). As the endothelial layer is formed quickly, there is no time for significant scar tissue to form over the stent.

WO03/065881 discloses antibody-coated stents. These attract EPC cells and promote the formation of a functional endothelial lining. However, an antibody is not necessarily specific, and it may react with other cells as well as its environment. A non-specific effect may be observed and the efficiency of the system is unclear.

Polyak et al., PNAS 2007, 105, 698-703, discloses the concept of targeting endothelial cells to a magnetic stent. The stent must be in the presence of a magnetic field in order to be magnetised (paramagnetic). Once magnetised, the stent attracts magnetised bovine aortic endothelial cells, promoting healing of the blood vessel into which it has been inserted.

Biosorbable stents have also been used to repair arteries after angioplasty. Examples of biosorbable stents are stents made from a magnesium alloy or polymers such as polylactic acid. Biosorbable stents are popular as they overcome problems of stent size mismatch, and can prevent lumen expansion. A feature of biosorbable stents is that they are difficult to visualise using X-rays. This can make stent placement difficult. However, it also means that these stents can be used with MRI scans. This is a unique feature of biosorbable stents.

WO2008/034030 discloses a magnetised bioerodible endoprosthesis. The endoprosthesis (which is a stent) has a magnetised portion to aid stent placement and a separate bioerodible portion for drug elution. The stent, in its entirety, is not bioerodible.

Although bioerodible stents are useful, they are not very effective at preventing restenosis, which can and does occur before the stent has degraded.

SUMMARY OF THE INVENTION

Biosorbable endoprostheses are not very efficient at preventing restenosis. The present invention overcomes this problem by providing an endoprosthesis, which is both biosorbable and magnetisable. Such materials were not previously thought to exist. This allows the endoprosthesis to attract magnetisable cells capable of repairing an artery.

According to a first aspect, the present invention is a biosorbable magnetisable endoprosthesis.

According to a second aspect, a kit comprises an endoprosthesis as defined above and magnetisable cells capable of repairing an artery, preferably as a combined preparation, for simultaneous, sequential or separate administration in therapy.

According to third and fourth aspects of the invention, an endoprosthesis as defined above is for therapeutic use in a patient also receiving cells as defined above. Alternatively such cells are for use in a patient fitted with such an endoprosthesis

DESCRIPTION OF PREFERRED EMBODIMENTS

The endoprosthesis may be a stent or similar prostheses. Preferably, the endoprosthesis is a stent.

The endoprosthesis of the invention is magnetisable, which allows it to attract magnetisable cells to its surface.

The endoprosthesis is biosorbable. Suitable biosorbable materials from which the endoprosthesis may be constructed are magnesium alloys, polymers including polylactones, and iron alloys. Preferably, the entire endoprosthesis is magnetisable and/or biosorbable. A material which is both magnetisable and biosorbable is an iron alloy. Alternatively, the endoprosthesis comprises separate biosorbable and magnetised portions.

In a preferred embodiment of the invention, at least a portion of the endoprosthesis can be absorbed by the body, such that structural integrity of the stent is lost between 6 and 12 months after placement of the stent in the body. By loss of structural integrity, it is meant that the original shape of the stent is lost. The stent may not have been completely absorbed by the body by the time structural integrity has been lost. In a preferred embodiment, at least 30% of the stent has been absorbed between 6 and 12 months after placement in the body. More preferably, that figure is at least 40%, 50%, 60%, 70%, 80% or 90%. It is believed that this allows optimum regeneration of the artery. Before being completely absorbed by the body, the magnetic properties of the endoprosthesis allow it to attract certain cells, to aid in the formation of a functional endothelium and prevent restenosis.

Biosorbable endoprostheses are known in the art. A known biosorbable endoprosthesis can be magnetised according to the description herein, to form a biosorbable magnetisable stent according to the invention. In a preferred embodiment, a stent is absorbed between 6 to 12 months after placement in the body. The skilled person is able to choose a suitable material and/or thickness of the material in order to achieve this.

An example of a biosorbable stent that can be used in the invention is disclosed in US 2012/0143318, which is incorporated herein by reference.

In a preferred embodiment, an endoprosthesis is made from a metallic material comprising a magnesium alloy consisting of at least 96% w/w of magnesium, at least 1% w/w, of manganese and at least 0.5% w/w of at least one metal of the rare earth group.

Preferably, rare earth metals in this context are scandium, yttrium and lanthanum as well as the elements of the periodic table of elements following lanthanum, i.e. so-called lanthanides. These elements are in particular cerium, praseodymium, neodymium, promethium, samarium, europium, gadolinium, terbium, dysprosium, holmium, erbium, thulium, ytterbium and lutetium, with preference being given to cerium.

According to the invention the metallic material of the implants may consist of solid structures, lattice structures, wire or fabric structures as well as of metal foam or porous metal.

Spongy or porous structures offer advantages in that they permit a higher resorption speed, with the existing pores being conducive to the ingrowth of the body's own tissue. This allows the use of magnesium sponge bodies as placeholders, for example for the treatment of fractures and to augment bone or other tissue of the body.

The structure and strength of the metallic material used for the inventive implants are adapted to suit their placement site and purpose, for instance as far as their mechanical properties and/or use as drug delivery systems are concerned.

The implants proposed by the present invention may consist altogether or partly of such a resorbable metallic material. Aside from the inventive resorbable metallic material such materials may be other resorbable or non-resorbable metallic or non-metallic materials. Such further components may in particular also be plastic materials consisting of a resorbable substance, for example a polylactide or polyglycolide.

Resorbable plastic materials of this nature are often used for the purpose of coating stents. Moreover, chitin and chitosan biopolymers can be used for coating purposes as well. Coatings frequently serve as substrate for medical substances which by this method are gradually released and dispensed into the surrounding area.

Preferably, the resorbable magnesium alloy according to the invention consists of 96 to 97.9% w/w of magnesium, 1.6 to 2% w/w of manganese and 0.5 to 2% w/w of rare earth metal. For this purpose, neodymium or cerium is preferably used as rare earth metal. In particular, a composition comprising 97.45% w/w of magnesium, 1.8% w/w of manganese and 0.75% w/w of cerium is preferred.

The biosorbability time can be controlled by adjusting the manganese content as desired, i.e. the lower the manganese content the higher the resorption speed.

The construction of biosorbable endoprostheses are known in the art. In an exemplary embodiment, stents may be cut from tubes manufactured from the relevant magnesium alloy, for example by means of an extrusion process.

Having cut the stent to size it can be crimped onto a dilatation balloon by means of a method known in the art and together with said balloon transferred to the placement site.

It will be understood by the skilled person that the endoprosthesis of the invention can be coated with a polymer material with a view to influencing their dissolving behavior or dispensing a medical substance out of the polymer layer. Such drug eluting stents (DES) have been known for a long time and in many cases provided with proliferation-inhibiting medical agents.

In a further preferred embodiment, maximal magnetic effect is present for a period of at least one week (and preferably about one week) after placement in the body. Preferably, further magnetism can be applied to the stent via magnet external to the body, or positioned within the oesophagus.

In a particularly preferred embodiment, the stent is constructed according to U.S. Pat. No. 7,691,142, which is incorporated herein by reference. This describes a stent, which has high stability, in particular radial strength, while allowing good utilization of material. The stent described in this publication has a tubular support frame which is expandable from an initial state to a support state. The support frame is made of ring segments which are arranged sequentially in longitudinal stent axis and formed by struts which are joined continuously in a wave-like manner in circumferential direction of the support frame. Adjacent ring segments are linked by differently long connectors with U-shaped compensating sections. All these compensating sections point in the same circumferential direction. Connectors of different length alternate in circumferential direction as well as in longitudinal stent axis.

The design of the stent described in U.S. Pat. No. 7,691, 142 is configured in such a manner that the immobile struts, which converge respectively with their ends in nodal points that act as friction-free joints, establish a type of self-stabilizing framework structure. Radial forces acting from outside to load the stent are absorbed in the nodal points and deflected there into the various strut directions.

For the purpose of this specification, the term "magnetic" includes "magnetisable", e.g. a stent whose properties can be influenced in situ. The stent can be paramagnetic or superparamagnetic.

As used herein, magnetisable is preferably "magnetic". For example, a magnetiseable stent is one that can be magnetised in situ. A magnetic stent is one that has been magnetised.

In a preferred embodiment, the endoprosthesis comprises a biodegradable polymer. Preferably, the biodegradable polymer is poly(lactic-co-glycolic acid) (PLGA). This polymer may be coated onto a biosorbable stent platform, i.e. a magnesium alloy stent. The biodegradeable polymer may comprise magnetisable particles, which are described in more detail below.

In a preferred embodiment, the endoprosthesis comprises a magnesium metal or alloy. A magnesium endoprosthesis may allow controlled degradation of the medical device in the body, with release of magnesium to the blood-contacting surface of the device.

In a preferred embodiment, the endoprosthesis comprises a biosorbable matrix, with magnetic particles embedded in, or situated on, the surface of the matrix.

Magnetic particles suitable for use in the invention are may comprise of any magnetic particles of which many are known, specifically, superparamagnetic iron oxide particles (SPIO), such as MRI contrast agents, magnetic beads or particles based on magnitite. In a preferred embodiment, the endoprosthesis is a stent, which preferably comprises magnetic iron nanoparticles embedded within a biodegradable matrix.

Preferably, the magnetic particles are magnetite, which is a ferrimagnetic mineral with chemical formula $Fe_3O_4$.

In a preferred embodiment, the magnetic particles, e.g. magnetite, is loaded onto a polymer, preferably PLGA. The polymer may form nanoparticles. The polymer may then be sprayed onto a biosorbable stent, or embedded within a biosorbable stent.

The endoprosthesis may also be drug-eluting. Examples of drugs which may be eluted by such a stent include antiproliferative drugs, such as sirolimus or paclitaxel.

A magnetic biosorbable stent embodying the invention can be constructed in a number of ways. In one embodiment a stent can be coated with a high concentration of a polymer-based biodegradable metallic/magnetisable coating. This will confer magnetism sufficient to attract magnetised cells to the stent. The stent may either be a high mechanical strength Mg-based biosorbable stent or a polymer based compound e.g. polyglycolic acid, poly-1-lactic acid, poly d,1-lactide/glycolide copolymer, polyorthoester or polycaprolactone.

A stent may comprise a polymer including a magnetisable material. The magnetiseable material can be provided as a coating on the polymer, or within the polymer body. The magnetisable material can be magnetised by applying a magnetic field or current. The magnetisable material preferably comprises magnetic particles, as defined above.

In addition, a stent may be coated with an iron oxide-based biodegradable polymer, or similar magnetisable coating, according to standard coating methods, should the required magnetic effect not be sufficient from the stent alone. Single-layer or multilayer systems may be created (e.g., a base coat, drug coat or topcoat layers or striations).

In a preferred embodiment, magnetite is used as the magnetic material to coat, or include in, the stent. Magnetite is a ferrimagnetic mineral with chemical formula $Fe_3O_4$.

Preferably, the endoprosthesis includes an X-ray maker, such as tungsten carbide.

In a preferred embodiment, the endoprosthesis comprises a delivery system for a gene therapy. For example, a viral gene transfer product may be within a coating, e.g. a polymer coating, or it may be present on the surface of the stent, using for example encapsulated viral particles.

In one aspect of the invention, a combination of an endoprosthesis as defined above and magnetisable cells capable of repairing an artery is provided. Such cells will be well known to those skilled in the art and include monocytes, multi and pluripotent stem cells and progenitor cells. In a preferred embodiment, the cells are endothelial progenitor cells.

Means for magnetising (or making magnetisable) such cells are known in the art, and include incorporating iron nanoparticles into the cells.

In one aspect of the invention, a kit is provided, which comprises a biosorbable magnetisable endoprosthesis and magnetisable cells capable of repairing an artery.

The endoprosthesis may be used for the prevention or treatment of a disease in the coronary arteries. It may be used for the repair or regeneration of the coronary arteries after angioplasty, for example for the prevention or treatment of restenosis. The stent may also be used for the repair or regeneration of other blood vessels. An endoprosthesis/kit of the invention may be useful in the therapy of stent thrombosis.

In one method of use, the endoprosthesis is a magnetisable stent which is placed in a coronary artery as part of an angioplasty procedure. Stem cells (preferably endothelial progenitor cells) are removed from the patient, labelled with magnetic particles (such as magnetic iron nanoparticles), or magnetised in another way and returned to the body, e.g. via injection. For example, the stem cells may have metal particles provided intracellularly or attached to their surfaces via antibodies. The stent will then attract the magnetic stem cells to the stent/artery wall interface, where they may promote the formation of a functional endothelial lining. The rapid formation of such a lining following angioplasty may be useful in the prevention of restenosis.

In an aspect of the invention, a method of treating of preventing restenosis or a disease of a blood vessel comprises fitting a patient with an endoprosthesis according to the invention and administering stem cells which have been magnetised. The endoprosthesis of the invention may have already been magnetised, in which case no further intervention is needed to effect the therapy. Alternatively, if this stent was not magnetised before placement in the body, it may be magnetised in situ to effect the therapy according to the invention.

Other cells that may be captured include a patient's own cells, taken from the body and transferred with a viral or non-viral vehicle expressing a beneficial gene, e.g. VEGF. When the cell thus manipulated is captured by the magnetised stent, it can express its beneficial protein locally in the artery.

The following Examples illustrate the invention.

Example

Magnetic particles suitable for use in the invention are constructed as follows, and loaded into PLGA to form nanoparticles. The resulting nanoparticles are sprayed onto a biosorbable stent (constructed from a magnesium alloy comprising 96 to 97.9% w/w of magnesium, 1.6 to 2% w/w of manganese and 0.5 to 2% w/w of a rare earth metal), to form a biosorbable magnetisable stent according to the invention. The designed biosorbability time-frame is achieved by adjusting the thickness of the stent accordingly.

Synthesis of magnetite: Iron acetylacetonate ($Fe(acac)_3$) (0.396 g, 1.56 mmol), oleic acid (1.47 mL, 4.64 mmol), oleylamine (1.02 mL, 3.09 mmol), 1,2-hexadecanediol (2.005 g, 7.76 mmol) and benzyl ether (10 mL) were added to a single-neck round bottom flask equipped with a magnetic stir bar and a condenser and deoxygenated for an hour. The reaction was gradually heated at 3° C./min to 200° C. and held at that temperature for 3 hours and then allowed to cool room temperature. A final black solution was observed. The reaction mixture was precipitated in ethanol and centrifuged twice. Ethanol was decanted and the product was dried via nitrogen purge leaving a black powder.

Preparation of magnetite-loaded into PLGA: PLGA is dissolved in chloroform (2 mL) and then added drop-wise to a vortexing solution of 5% poly-vinyl alcohol (PVA) (4 mL) and the resulting mixture was sonicated three times for 10 s at an amplitude of 38% (TEKMAR VCW 400 W). The mixture was then added drop-wise to 100 mL of 0.2% PVA and left stirring for 3 h to evaporate the solvent. Particles were collected by centrifugation at 12,000 RPM for 10 min at 4° C. and then washed three times with de-ionized water. The particles were lyophilized and stored at −20° C. until use. Particles functionalized on the surface with avidin were prepared in identical fashion with avidin-palmitate incorporated into the 5% PVA solution. Nanoparticles that encapsulating C-6 and functionalized with avidin were manufactured using a modified double emulsion variation of the water-oil-water technique. Nanoparticles encapsulating magnetite and MTX (dissolved in DMSO) were prepared using a single emulsion. Nanoparticles encapsulating magnetite and Clod were manufactured in a similar fashion using a double emulsion, water-oil-water technique.

The invention claimed is:

1. A biosorbable magnetisable endoprosthesis, comprising:
    i) a magnesium alloy; and
    ii) magnetic particles comprising iron within a biosorbable material comprising a biosorbable polymer,
   wherein:
    iii) a portion of the endoprosthesis can be absorbed by the body such that the structural integrity of the endoprosthesis is lost between 6 and 12 months after placement in the body; and
    iv) the endoprosthesis is configured such that it may attract magnetisable cells capable of repairing an artery to its surface,
   wherein (a) the magnesium alloy consists of at least 96% w/w of magnesium, at least 1% w/w of manganese and at least 0.5% w/w of at least one metal of the rare earth group, and/or (b) the magnetic particles are formed from an iron oxide-based biodegradable polymer.

2. An endoprosthesis according to claim 1, which is a stent.

3. A kit comprising a biosorbable magnetisable endoprosthesis and magnetisable cells capable of repairing an artery, wherein the biosorbable magnetisable endoprosthesis, comprises:
    i) a magnesium alloy; and
    ii) magnetic particles comprising iron within a biosorbable material comprising a biosorbable polymer,
   and wherein:
    iii) a portion of the endoprosthesis can be absorbed by the body such that the structural integrity of the endoprosthesis is lost between 6 and 12 months after placement in the body; and
    iv) the endoprosthesis is configured such that it may attract magnetisable cells capable of repairing an artery to its surface
   wherein (a) the magnesium alloy consists of at least 96% w/w of magnesium, at least 1% w/w of manganese and at least 0.5% w/w of at least one metal of the rare earth group, and/or (b) the magnetic particles are formed from an iron oxide-based biodegradable polymer.

4. A kit according to claim 3, wherein the cells are progenitor cells, preferably endothelial progenitor cells.

5. A kit according to claim 3, wherein the cells comprise iron.

6. A kit according to claim 3, as a combined preparation for simultaneous, separate or sequential use in therapy.

7. An endoprosthesis according to claim 1, wherein the magnesium alloy consists of at least 96% w/w of magnesium, at least 1% w/w of manganese and at least 0.5% w/w of at least one metal of the rare earth group.

8. An endoprosthesis according to claim 1, wherein the magnetic particles are formed from an iron oxide-based biodegradable polymer.

9. An endoprosthesis according to claim 1, wherein (a) the magnesium alloy consists of at least 96% w/w of magnesium, at least 1% w/w of manganese and at least 0.5% w/w of at least one metal of the rare earth group, and (b) the magnetic particles are formed from an iron oxide-based biodegradable polymer.

10. A kit according to claim 3, wherein the magnesium alloy consists of at least 96% w/w of magnesium, at least 1% w/w of manganese and at least 0.5% w/w of at least one metal of the rare earth group.

11. A kit according to claim 3, wherein the magnetic particles are formed from an iron oxide-based biodegradable polymer.

12. A kit according to claim 3, wherein (a) the magnesium alloy consists of at least 96% w/w of magnesium, at least 1% w/w of manganese and at least 0.5% w/w of at least one metal of the rare earth group, and (b) the magnetic particles are formed from an iron oxide-based biodegradable polymer.

* * * * *